United States Patent
Ruoff et al.

(10) Patent No.: US 8,504,391 B2
(45) Date of Patent: Aug. 6, 2013

(54) PERSON CENTRIC INFECTION RISK STRATIFICATION

(75) Inventors: Chad Barrett Ruoff, Lee's Summit, MO (US); Hugh Ryan, Lee's Summit, MO (US); Lori Cross, Kansas City, MO (US)

(73) Assignee: Cerner Innovation, Inc., Lenexa, KS (US)

( * ) Notice: Subject to any disclaimer, the term of this patent is extended or adjusted under 35 U.S.C. 154(b) by 469 days.

(21) Appl. No.: 12/651,112

(22) Filed: Dec. 31, 2009

(65) Prior Publication Data

US 2010/0198611 A1  Aug. 5, 2010

Related U.S. Application Data

(63) Continuation-in-part of application No. 11/627,045, filed on Jan. 25, 2007.

(51) Int. Cl.
 G06Q 10/00  (2012.01)
 G06Q 50/00  (2012.01)

(52) U.S. Cl.
 USPC .................................................. 705/3; 705/2

(58) Field of Classification Search
 USPC ........................................................ 705/2–3
 See application file for complete search history.

(56) References Cited

U.S. PATENT DOCUMENTS

| 5,800,347 | A | * | 9/1998 | Skates et al. | 600/300 |
|---|---|---|---|---|---|
| 7,258,667 | B2 | * | 8/2007 | McNair | 600/300 |
| 7,853,407 | B2 | * | 12/2010 | Yancey, Jr. | 702/19 |
| 8,224,670 | B2 | | 7/2012 | Tarkka et al. | |
| 2002/0103671 | A1 | * | 8/2002 | Pederson et al. | 705/2 |
| 2008/0050829 | A1 | * | 2/2008 | Ivey et al. | 436/63 |
| 2008/0126124 | A1 | * | 5/2008 | Schechter | 705/2 |

OTHER PUBLICATIONS

Cosgrove et al., "The Impact of Methicillin Resistance in *Staphylococcus aureus* Bacteremia on Patient Outcomes: Mortality, Length of Stay, and Hospital Charges," Infection Control and Hospital Epidemiology, vol. 26, No. 2, Feb. 2005, pp. 166-174.*
Final Office Action in U.S. Appl. No. 11/627,045, mailed Mar. 31, 2010, 14 pages.
Non Final Office Action in U.S. Appl. No. 11/327,045, mailed Nov. 15, 2012.

* cited by examiner

*Primary Examiner* — Michael Fuelling
(74) *Attorney, Agent, or Firm* — Shook Hardy & Bacon LLP (57) ABSTRACT

Invoking of one or more clinical orders for a particular patient is driven by an infection risk stratification. According to an associated method, infection risk factors for a patient are assessed. The method also includes determining correlations between patient data and two or more particular categories of infection risk associated with the infection risk factors, stratifying infection risk for the patient based on the correlations determined, and determining specific clinical orders relevant for the particular patient based on the stratification.

15 Claims, 6 Drawing Sheets

PERSON CENTRIC INFECTION RISK STRATIFICATION

CROSS-REFERENCE TO RELATED APPLICATIONS

This application is a continuation-in-part of U.S. Publication No. 2008/0183499 filed Jan. 25, 2007, entitled "System And Method For Determining A Person Centric Infection Risk Associated With Encountering A Healthcare Provider", and which application is hereby incorporated by reference in its entirety.

STATEMENT REGARDING FEDERALLY SPONSORED RESEARCH OR DEVELOPMENT

Not applicable.

TECHNICAL FIELD

The present invention relates to computing environments. More particularly, embodiments of the present invention relate to methods and systems for use in, e.g., a patient care computing environment, the methods and systems for determining infection risk for a patient associated with encountering a healthcare provider. Further embodiments of the present invention relate to a user interface for displaying the infection risk.

BACKGROUND OF THE INVENTION

Individuals in need of medical attention for a variety of ailments or conditions typically seek clinical treatment from a healthcare provider. Such treatment may include a combination of procedures, medications or other therapies to stabilize and/or improve the health of an individual or patient. However, the process of providing clinical treatment brings with it the risk of side effects. One such side effect of significant concern when patients seek procedure-related treatments from a healthcare provider is infections. For instance, with inpatient or outpatient surgical procedures, as well as intensive care unit (ICU) stays, the risk of infection to the patient can be high. Whether resulting from clinical issues such as contaminated equipment, individual patient health conditions, or other factors, infections can have a serious impact on the stability of a patient's health status and affect their ability to recover from a health condition. As a result, infections related to healthcare treatment delivery represent an increased risk to public health, and create a significant clinical and financial burden to our society. It has been reported that more than 90,000 persons die annually from these types of infections resulting in a cost to our economy of more than $5 billion annually.

Historically, precautionary measures taken by healthcare providers or clinicians to mitigate the risks of infection have varied widely depending on the type of medical procedure performed, clinician training or preferences, healthcare provider policies, and government regulations. However, the risk of contracting an infection also varies widely depending on the individual patient and type of procedure performed for the patient. Therefore, because of the varying risk of contracting an infection and variety of steps taken to mitigate this risk, clinicians must often analyze an expansive set of information at the point of care to ascertain the potential risk level for a given patient to contract an infection.

Healthcare providers have attempted to establish a generalized guide for determining the level of infection risk for patients seeking clinical treatment in a given facility or system. As one example, the following formula has been widely used as a baseline for calculating the risk of infection:

$$\left[\frac{1}{(\text{Patients} \times \text{incidence \%})}\right] \times 100$$

where Patients=the number of annual inpatient admissions for a specific facility or system and incidence %=the number of incidents of infection expressed as a percentage. For example, assume that a clinic admits 16,458 patients in a given year and the incidence of infection for that clinic in that year is 5.7%. The calculated risk of infection for any given patient receiving treatment, according to the formula, would be 0.1%, without regard for the particular patient's medical history, current condition, or treatment that they are undergoing.

This baseline infection risk formula has considerable limitations, since many circumstances surrounding the delivery of care are not taken into consideration. Furthermore, it becomes difficult to monitor a given patient's infection risk over time. For instance, one general assumption is that infection risk increases the longer a patient remains in the hospital or other healthcare facility. Clinicians are essentially left to approximate a particular patient's overall infection risk, and determine whether that risk will increase or decrease during a treatment period. This makes it difficult to implement an infection risk control plan best suited for the patient and creates numerous opportunities for error.

BRIEF SUMMARY OF THE INVENTION

Embodiments of the present invention provide a system and method of determining a risk of infection for a particular patient associated with encountering a healthcare provider. The infection risk may be quantified as a value that changes over time due to variance in the infection risk factors for the patient.

In one aspect, a method in a computing system environment is presented for determining a patient's infection risk associated with a specific healthcare provider encounter. In this method, infection risk factors for a particular patient are first assessed. These patient-centric infection risk factors are then compared to a set of benchmark infection risk factors derived from historical patient outcomes data. Based on the results of the comparison, which optionally may include assigning weighting factors to certain benchmark infection risk factors, the infection risk assessment for the particular patient is determined and displayed. The infection risk assessment may involve determining particular infection risk values at previous, current or future points in time depending on the particular patient-centric infection risk factors that are considered. Additionally, updated infection risk factors may subsequently be collected and compared to the set of benchmark infection risk factors to determine an updated patient infection risk assessment.

The infection risk assessment may optionally be determined prior to or during the particular patient's encounter with the healthcare provider (e.g., in preparation for or during an inpatient stay for a specific treatment), or alternatively at a post-encounter time point. Further, the infection risk assessment may optionally provide a future prediction of infection risk over time based on clinically relevant information currently possessed.

By utilizing benchmark infection risk factors as evidence-based clinical data, a more meaningful infection risk assessment for a given patient may be derived. A treating clinician can then utilize the infection risk assessment to select a specific infection risk control plan with a greater probability of positive outcomes for the patient. Additional advantages and features of the invention will be set forth in part in a description which follows, and in part will become apparent to those skilled in the art upon examination of the following, or may be learned by practice of the invention.

BRIEF DESCRIPTION OF THE SEVERAL VIEWS OF THE DRAWING

The present invention is described in detail below with reference to the attached drawing figures, wherein.

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present invention provides a system and method of determining the risk of infection for a particular patient associated with encountering a healthcare provider. The present invention also provides a computer-readable medium having computer-executable instructions for performing the method of determining a particular patient's infection risk. The present invention further provides a user interface as a display region for presenting a graphical representation of an infection risk values set for a particular patient based on a specific encounter by the patient with a healthcare provider. The display region is also configured to present a time factors set associated with the infection risk values set, where each time factor correlates with one of the infection risk values.

Figure 1:
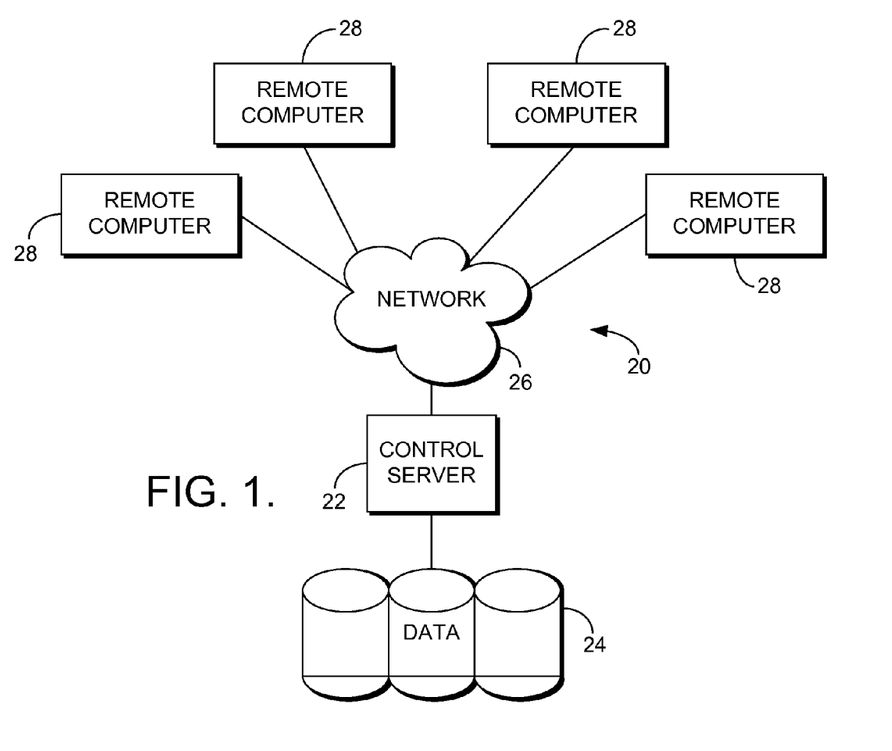
FIG. 1 is a block diagram of an exemplary computing system environment suitable for use in implementing the present invention.

Referring to the drawings in general, and initially to FIG. 1 in particular, an exemplary computing system environment, for instance, a medical information computing system, on which the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer readable media, for instance, database cluster 24. Computer readable media can be any available media that may be accessed by control server 22, and includes volatile and nonvolatile media, as well as removable and nonremovable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage device, or any other medium which can be used to store the desired information and which may be accessed by control server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media The computer storage media discussed above and illustrated in FIG. 1, including database cluster 24, provide storage of computer readable instructions, data structures, program modules, and other data for control server 22.

The control server 22 may operate in a computer network 26 using logical connections to one or more remote computers 28. Remote computers 28 may be located at a variety of locations in a medical or healthcare environment, for example, but not limited to, clinical laboratories, hospitals and other inpatient settings, ambulatory settings, medical billing and financial offices, hospital administration settings, home health care environments, and clinicians' offices, or any other healthcare provider settings. Clinicians, as referred to herein, may include, but are not limited to, an infection control professional, a treating physician or physicians, specialists such as surgeons, radiologists, and cardiologists, emergency medical technicians, physicians' assistants, nurse practitioners, nurses, nurses' aides, pharmacists, dieticians, microbiologists, and the like, and aides or assistants thereto. Remote computers 28 may also be physically located in non-traditional medical care environments so that the entire health care community may be capable of integration on the network. Remote computers 28 may be personal computers, servers, routers, network PCs, personal digital assistants (PDA), peer devices, other common network nodes, or the like, and may include some or all of the elements described above in relation to the control server 22.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or all of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. The control server 22 and/or remote computers 28 may include other peripheral output devices, such as speakers and a printer.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

In modern clinical settings, there is often an electronic record, for instance, an electronic medical record (EMR) associated with each patient present at a hospital or clinic. For example, one particular electronic medical record format is generated by Cerner Millennium available from Cerner Corporation of Kansas City, Mo. Electronic medical records are typically designed to contain various types of data about an individual patient, a partial list of which includes: patient identifying and demographic information; insurance and financial information; patient health status, such as observed conditions of the patient (e.g., physiological conditions such as blood pressure, oxygen saturation levels in blood, or other "vital signs" and history), medications taken and current immunizations and immunization status, laboratory tests results, food and drug allergies, diagnoses and assessment by various clinicians; and care documentation (including a listing of clinicians that are currently providing or that have provided care to the patient and documentation of various events occurring during the care process). Any or all of the information in the electronic medical record may be organized into one or more structured charts within the record, and as one example, the EMR may take the form of a continuity of care record (CCR) or community health record (CHR) including a personal health record (PHR) maintained by a particular patient. In addition to a patient's health record, health data may also be extracted for a database of medical claims for the patient to form a medical record. The claims database is typically compiled by claims payers, such as insurance companies, who receive the claims from a clinician or other healthcare provider. It should be understood, however, that the term "medical record", "health record" or "electronic medical record" in particular, should not be interpreted to be limited to any type of computer-readable format or record, but includes any electronically-stored data structure containing information relative to at least one specific patient and from which information may be viewed and/or extracted by various components of the computing system environment 20, such as remote computers 28. As one example, a medical or health record may contain a medication administration record (MAR) detailing medications that have been administered to a patient. Additionally, it should be noted that the terms "patient", "person" and "individual" will be used interchangeably throughout the application and are not meant to limit the nature of the referenced individual nor imply any particular relationship between the individual in question and clinicians or other persons performing an infection risk determination or any other described processes. Also, the aforementioned may be populated into a community data warehouse (or national/regional research database) for outcomes, discovery and benchmarking to support incorporation of better evidence to the care process.

In one embodiment, database cluster 24 is configured to store patient data. Techniques for storing, organizing, and retrieving patient data in database cluster 24 are well-known to those skilled in the art, and need not be discussed at length herein.

In one embodiment, patient data may include an order, such as a request by a clinician for an action related to the patient, referred to herein as a "clinical order" or simply an "order." The action can be the initiation of a diagnostic test, the administration of a medication, a defined diet, or other health care-related action. Orders are captured by clinical information systems by a variety of means—direct user entry (computerized provider order entry (CPOE)), indirect entry by an intermediary, for example a verbal or written request that is conveyed to a nurse, the lab or pharmacy; or by an interface from another information system.

Orders can be placed singly or as a set. A single order would be ordering an individual medication or a serology test, while a set has multiple orders. An exemplary order set is a Chem 20, in which a number of discrete laboratory tests are ordered through a single action. Placing an order in the system has a variety of implications, including its formal presence in the clinical workflow and the triggering of billing-related events.

In one embodiment of the invention, an order within a set of orders can be designated as optional. Unlike conventional orders, optional orders are not placed in the system by default when the set of orders is placed. An optional order can be activated at the time the order set is placed or later in the process. If the user is ordering a set of orders associated with optional orders, the user is prompted to activate the optional orders. Optional orders that are selected are activated and added to the set of orders. Optional orders that were not activated when ordering the order set are displayed with the set of placed orders, allowing them to be activated later if necessary. A technologist or scientist can activate optional orders based on the findings associated with other orders in the case, allowing for flexibility of the testing path. In another embodiment, the ability to designate whether the activation of the order can occur at order time or only after the order sets have been placed is provided.

Figure 2:
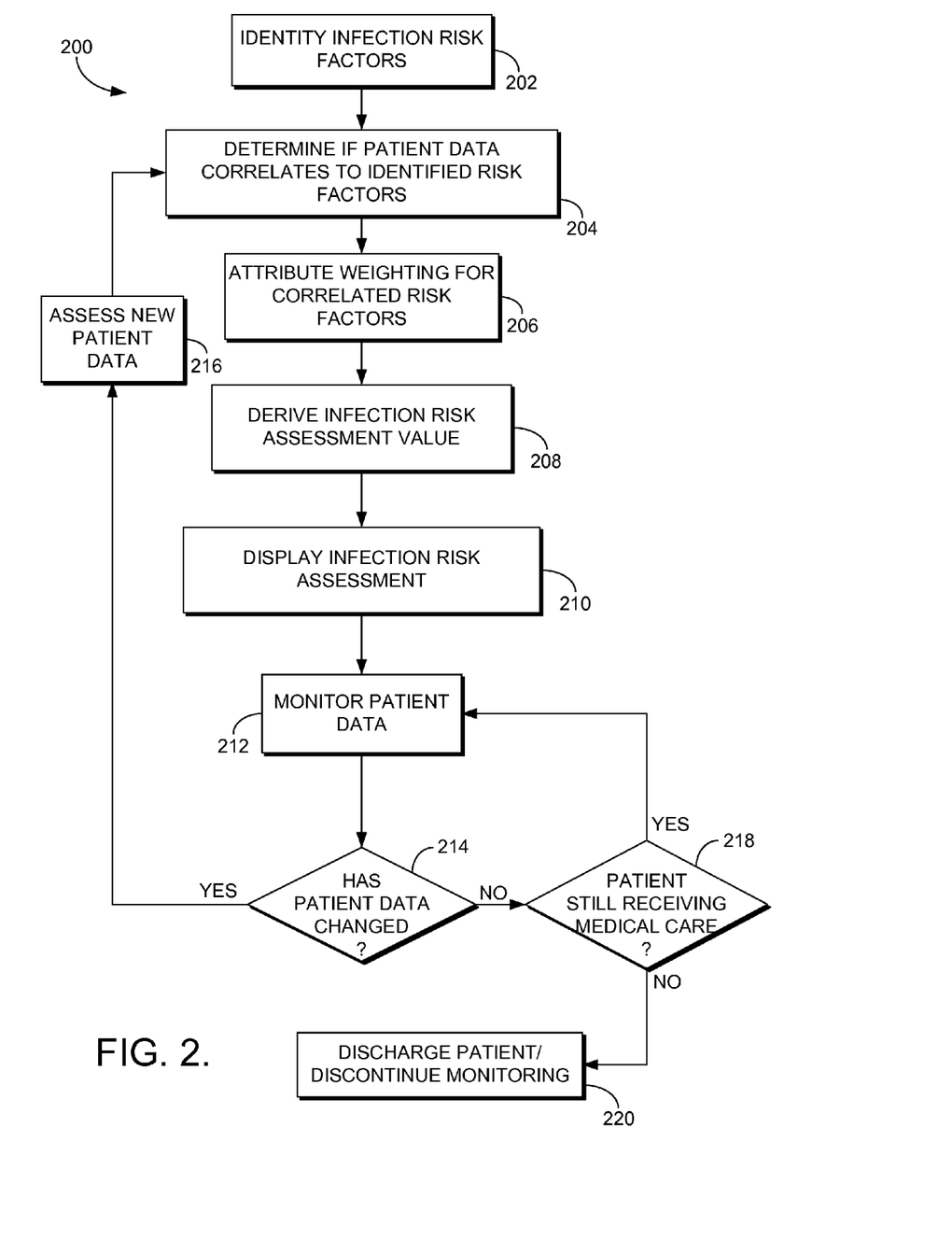
FIG. 2 is a flow chart representative of a process for determining infection risk for a particular patient encountering a healthcare provider in accordance with an embodiment of the present invention.

Referring now to FIG. 2, a flow chart representative of a computerized method of determining infection risk for a particular patient is depicted generally as reference numeral 200. The infection risk determination method 200 may be implemented on the above-described exemplary medical information computing system 20 (FIG. 1) and, by way of example only, may be utilized by a clinician to perform an infection risk determination for a particular patient. Also, an infection control professional may utilize infection risk determinations for multiple patients to monitor populations.

The infection risk determination method 200 is applicable to patients encountering the healthcare system where clinical treatment is sought. As one example, the clinical treatment may involve a medical procedure in an inpatient or outpatient setting. The infection risk for a patient may also be determined prior to, during or after a particular patient's actual encounter with the healthcare system, taking into account information such as patient-related health data and clinical procedure-related data. For instance, an infection risk assessment may be determined by the method 200 as a predictive infection risk assessment for a future point in time (e.g., for a patient once they reach post-operative recovery) when information is provided about what the patient will be encountering and/or regarding other clinical data that facilitates making such a predictive assessment. Alternatively, the infection risk assessment may focus on current or previously documented patient-related health data to enable an assessment to be made for a specific point in time when at least a portion of the relevant patient-related health data was captured (e.g., at the present point in time, a previous date and time, etc.).

Various circumstances surrounding the delivery of care to a particular patient may trigger the initiation of the method. For instance, the process may be initiated when a particular patient is scheduled to encounter or is actually encountering a healthcare provider (e.g., based on patient-specific input received on remote computer(s) 28 of computing system 20). A clinician may also submit a request to computing system 20 at any specific point in time when an infection risk determination is desired. It should be understood that the clinician's request for an infection risk determination may optionally include a requested time/date point, which is not necessarily the time at which the request is submitted. The clinician may desire, for example, to understand the patient's infection risk at the time the patient encounters surgery, for comparison with the current infection risk after the surgery such as the current time. The assessment of the patient's infection risk factors would then focus on the patient-related health data documented since the previous date and time.

Once initiated, at a first step 202 infection risk factors are identified. In an embodiment, a knowledge base stored in database 24 (FIG. 1) is accessed to identify the risk factors or variables for determining infection risk. A standard set of risk factors may be accessed, or, alternatively, one of a number of sets of risk factors may be selected depending on the patient-specific, provider-specific or other data relevant to the particular transaction, such as from a standard set of factors and/or from the research database described above. A specific example is set forth in FIGS. 4A-B as described below. A non-exhaustive list of typical infection risk factors includes: ICD-9 codes for specific diagnoses made (e.g., chronic diseases or conditions such as diabetes or cancer); social history or demographic information such as age (particularly for young or elderly patients), gender, body mass index number/obesity and smoking habits; information identifying or related to the procedure being undertaken; surgical wound classification; any immunosuppressive conditions, time since being admitted into a healthcare facility; location(s) within a specific facility where the patient has spent time, especially locations where drug-resistant organisms have been found (e.g., in a nearby patient room); current infections; length of stay overall or at a specific location; laboratory test values (e.g., serum urea, creatinine, glucose levels, etc.); length of intubation and/or mechanical ventilation assistance; use of steroids; chemotherapy; and timing of prophylactic antibiotics administration prior to a surgical procedure. Each facility may also have infection rates that are factors to determining the infection risk. Each factor may be classified and categorized and weighted differently as described below with reference to the categories of major and other diagnosis. Whether relying on general evidence-based knowledge sources or provider/facility specific patient outcomes data in compiling the benchmark infection risk factors, the associated quantified infection risk probabilities may be associated with the infection risk factors through a relational data structure (e.g., a relational database) that is searchable based on the particular patient's infection risk factors gathered.

As a matter of illustration, if a diabetic patient was admitted to a hospital two days ago, and had surgery yesterday to repair a broken femur, a documented infection in the patient's foot two years ago does not have particular relevance to their infection risk on the current date, unless the same infection was diagnosed in the last few days. On the other hand, other health data may be relevant to determining the infection risk at another point in time. For example glucose levels documented for the patient prior to surgery are relevant for determining infection risk on the date of surgery. In another example, the expected post-surgical recovery time a patient will likely spend in an ICU is relevant to estimate the predictive level of infection risk over that recovery time.

Continuing with the method 200, at step 204, a determination is made regarding the degree of data correlation between the identified risk factors and the data. Specifically, the patient-specific data in the medical record are queried based on the identified risk factors. In order to correlate, the patient-specific data in the medical record must be timely and contextually relevant as defined by the knowledge base.

The comparison of the patient's infection risk factors with the benchmark infection risk factors, therefore, involves looking for correlations therebetween. The benchmark infection risk factors may have quantified infection risk probabilities associated therewith, such as percentage rates of infection that have been documented. For example, a risk factor for a class III wound alone (contaminated, traumatic wound, or operation with a major break in sterile technique) may be associated with a 10-17% rate of infection, while a risk factor for a class III wound specifically on a patient who is a diabetic may be associated with a somewhat higher rate of infection.

Upon correlating the patient's infection risk factors with infection risk factors, at step 206, a weighting factor may be applied to each risk factor. This weighting factor can increase or decrease the significance of a quantified infection risk probability, or if no infection risk probability is associated with a given risk factor, then the weighting factor may be applied against a default value. To illustrate, an elderly patient undergoing a surgical procedure has a given baseline infection risk. However, the risk may be less relevant than the fact that the patient has been diagnosed with a serious chronic disease, and a stronger weighting factor (e.g., a 2.0) is applied to the chronic disease risk factor correlation than a risk factor associated with the patient's age and/or surgical procedures undertaken (e.g., a 1.0). The utilization of weighting factors may also become advantageous the more infection risk factors are correlated. As many risk factors provide a differing probability of effect depending on what other risk factors to which the patient is exposed, weighting factors serve to ensure that more of the circumstances surrounding risk infection are considered for a given patient, which may not be reflected in historical patient outcomes data from general evidence-based knowledge sources. Furthermore, a specific healthcare provider or health system may decide to weigh certain risk factor correlations differently based on previous experience with infection risk assessments or in an effort to focus on certain clinical practices for infection risk control.

The weighted risk factor correlations are then aggregated together through a summation to create an infection risk assessment value for the patient, in step 208. The value may be, for example, a numerical index value or percentage risk of infection. However, the infection risk assessment value may be in the form of any type of value that conveys infection risk, such as a graduated scale of risk (e.g., low-medium-high), among others. The infection risk assessment value is associated with a specific time. Otherwise, the infection risk assessment value is associated with a time factor referring to when the relevant patient-specific data was captured, or in the case of a predictive infection risk assessment for a future date and/or time, with patient infection risk factors derived from information about what the patient will be encountering (e.g., a scheduled procedure or expected recovery situations) and/or regarding other clinical knowledge that facilitates making such a predictive assessment.

Upon creating an infection risk assessment value for the patient associated with a particular date/time, steps 202 through 208 may be repeated if desired for determining infection risk assessment values associated with additional dates/times. In step 210, a graphical representation of each infection risk assessment value is presented in an exemplary user interface 300 shown in FIG. 3. User interface 300 includes a display area 302 providing a graphical representation of each infection risk assessment value and associated times. More specifically, a line graph 304 represents, for a particular patient, the plot of each infection risk assessment value as a percent risk of infection versus patient days in the healthcare facility. The dashed box 306 around "Day 3" designates the current date, with the historical infection risk assessment values shown for "Day 1" and "Day 2" and predictive infection risk assessment values shown for days past "Day 3". Providing such a representation gives a visual indication of potential risk to caregivers throughout the patient encounter, and also facilitates understanding trends in infection risk for a given patient over time. The different shaded regions 308 of the display area 302 represent relative risk levels, in this example the levels are divided into three sections, less than 2.5%, 2.5%-5%, and greater than 5% risk of infection. However, the ranges cited in this example are merely representative of practical delineations for infection risk and not meant to limit the invention as those of skill in the art can appreciate. Additionally, although the line graph 304 is shown plotted as a function of patient days as the relevant time factor, this timeframe can also be expressed in other intervals depending on the situation. For instance, as patient conditions rapidly change during and after a surgical procedure, time factor this chart may be better represented as a function of hours instead of days. Also, it should be understood that the time factors may be represented as specific points in time when a clinician requested an infection risk determination be conducted.

Figure 3:
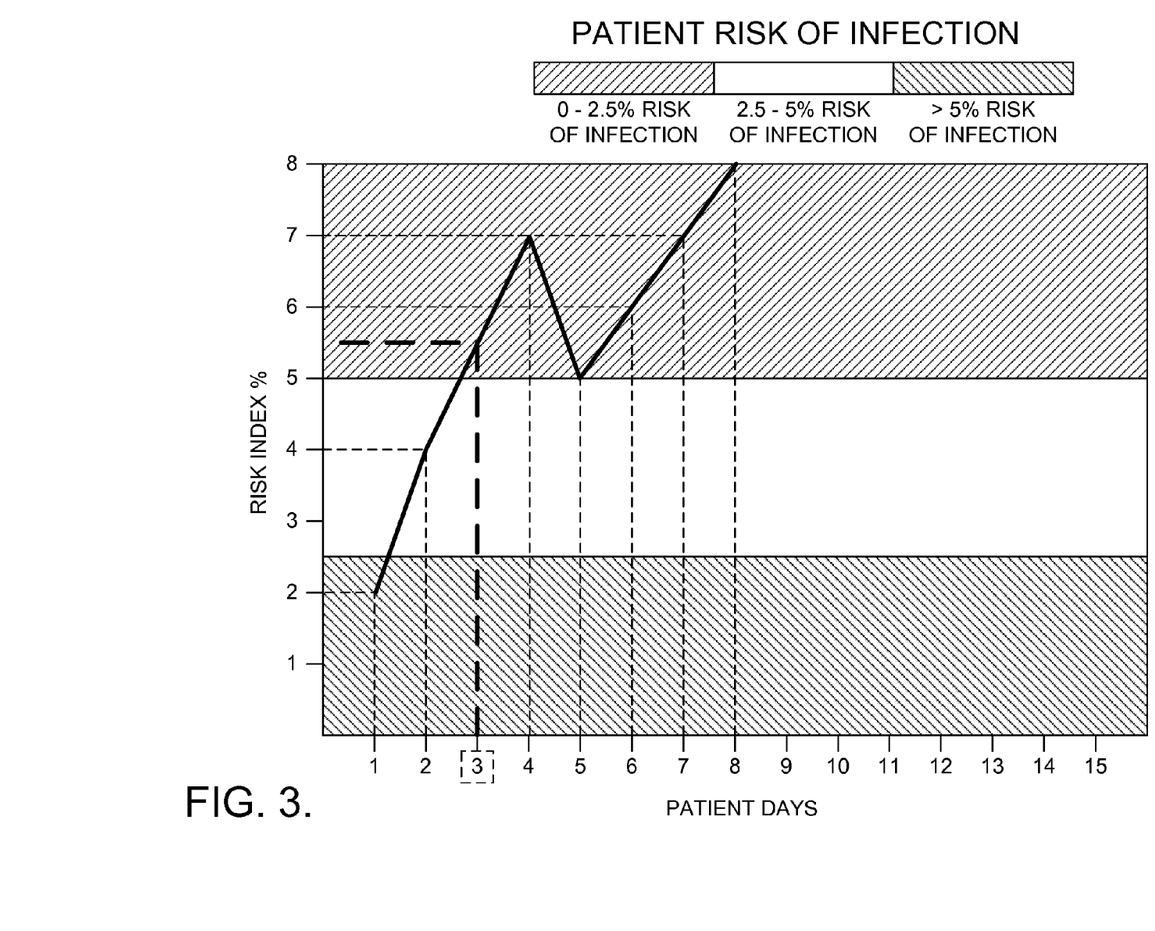
FIG. 3 is an exemplary display region of a user interface presenting a graphical representation of derived infection risk values plotted at various points in time.

The plotting of the infection risk assessment values through "Day 8" in line graph 304 is predicated on estimating the length of a course of treatment for the patient and an understanding of what infection risk factors are relevant during that period of time. For instance, if the patient is having surgery on "Day 4", and the plan of care calls for administering to the patient prophylactic antibiotics, it may be predicted that the percent risk of infection may be lower on the day after the surgery, "Day 5". At the same time, if the surgery is considered a complicated or invasive procedure, likely requiring an extended post-surgical stay in an ICU, then the infection risk may be predicted to climb daily due to historical outcomes data showing that relatively high rates of infection risk are correlated with extended ICU stays.

In conjunction with the display of the graphical representation of infection risk assessment values in user interface 300, step 210 may also involve displaying one or more recommended clinical practices or standard of care guidelines for mitigating infection risk based on the particular infection risk factors and patient's infection risk factors from step 204. Various evidence-based electronically searchable knowledge sources, such as the Critical Outcomes database, knowledge sources established by a specific health system, governmental knowledge sources (e.g., Centers for Disease Control, the Food and Drug Administration, etc.), among others, may serve as sources for standard of care guidelines or the like. The relevant information from the sources is extracted and may be presented on user interface 300 in any type of display area (e.g., adjacent to the line graph 304 and shaded regions 308 of display area 302) so that a clinician treating the patient can decide whether to implement the recommended clinical practices.

In step 212, the particular patient's electronic health record or other source of patient-specific data relevant to an infection risk determination is monitored to look for changes in infection risk factors. This monitoring may take place at pre-established time intervals (e.g., daily at a certain time), in real time or at any other time such as entry of new information or ad hoc request for an update to the risk determination. In an embodiment, the monitoring occurs when a clinician requests to see current infection risk assessment values for a particular patient in user interface 300 (e.g., a request including patient-specific input received on remote computer(s) 28 of computing system 20). Subsequently, in step 214, a determination is made as to whether any of the relevant data have changed, based on the monitoring activity of step 212. If there has been a change in infection risk factors, then in step 216, these data are assessed, and the method continues with step 204 so that an updated infection risk assessment value associated with a current time factor can be established in step 208. Alternatively, if in step 214 no changes in patient data are found, then in step 218, a determination is made as to whether the particular patient is still receiving medical care or treatment from the healthcare provider. This determination may focus on, for example, whether the patient has been discharged from a particular facility, or is no longer under the direct supervision of clinicians at the healthcare provider, all of which may be determined from the patient's electronic health record. If the particular patient is still receiving medical care, then the process returns to step 212 for continued monitoring of changes in infection risk factors. If the patient is no longer receiving medical care, then in step 220 monitoring for changing infection risk factors ceases and patient discharge is noted.

Figure 4A:
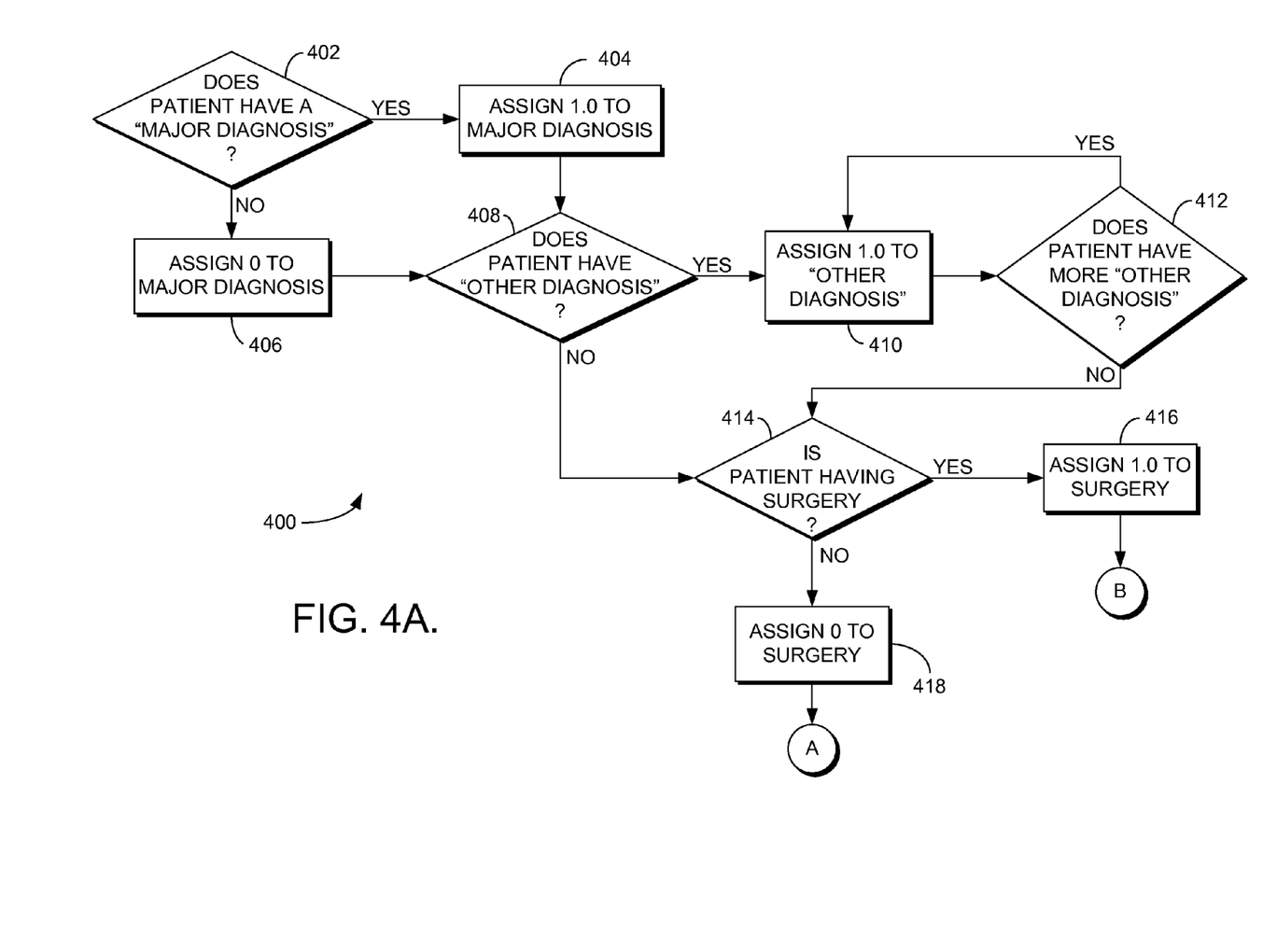
FIGS. 4A and 4B depict a flow chart representative of an exemplary algorithm for deriving an infection risk value for a particular patient capable of implementation within the process of FIG. 2.
Figure 4B:
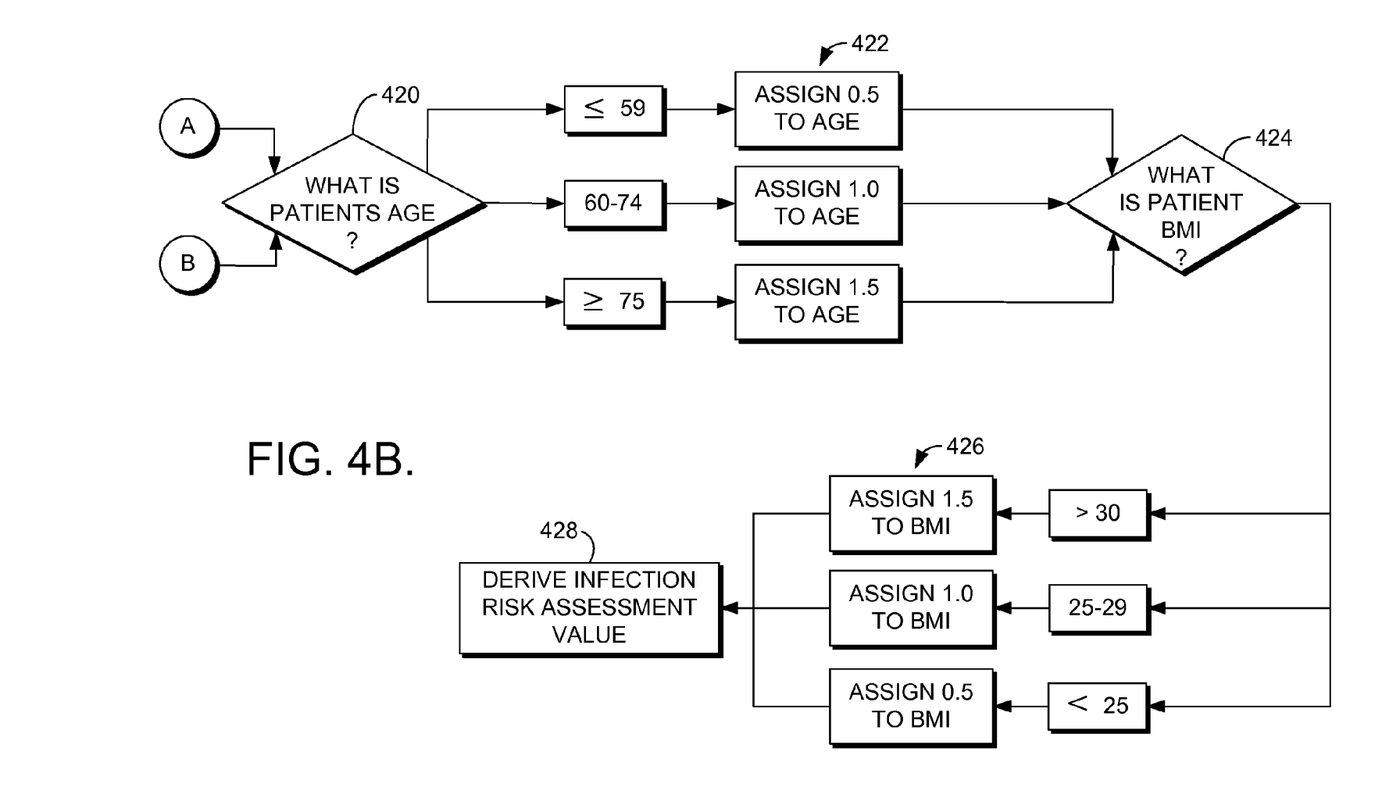

One practical example of an infection risk determination process 400 implemented in method 200 is depicted in the flow chart of FIGS. 4A and 4B. The process 400 focuses on certain exemplary infection risk factors for a patient, implements a weighting scheme based on infection risk factors, and then establishes an infection risk value for the patient that may be associated with a particular time factor (e.g., the current date/time) and displayed on user interface 300.

With reference to FIG. 4A, process 400 begins at step 402, a determination is made as to whether the patient has at least one major diagnosis that is currently valid such as Cirrhosis. If the patient does have a major diagnosis, then in step 404, a 1.5 weighting factor is assigned to the "major diagnosis" element. Otherwise, in step 406, a 0 weighting factor is assigned to major diagnosis element. At step 408, another determination is made as to whether the patient has other diagnoses that are currently valid, such as chronic diseases (e.g., diabetes and/or cancer). If a patient does have "other diagnosis", then a 1.0 weighting factor is assigned to the other diagnoses element in step 410 and the process of determining if the patient has "other diagnoses" repeats, as shown by step 412, until all additional "other diagnoses" are tallied. Each "other diagnosis", while important to an infection risk determination, is not as significant as whether the person has at least one "major diagnosis", and thus each additional diagnosis has a lower weighting factor. Returning to step 408, if the patient has no "other diagnosis", then the process continues at step 414. Also, once all additional "other diagnoses" are tallied from step steps 410 and 412, the process continues at step 414.

The next step, step 414 involves determining whether the patient is undergoing a surgical procedure. If so, then a 1.0 weighting factor is assigned to the surgery element in step 416. If on the other hand no surgical procedure will be undertaken, then a 0 weighting factor is assigned to the surgery element in step 418.

Turning to FIG. 4B, process 400 continues with step 420 where a determination is made as to the patient's age, so that different weighting factors may be assigned depending on the patient's age in step 422. Clinical knowledge has shown that age becomes an increasingly important infection risk factor as a patient becomes elderly patients, often because elderly patients have a weaker immune system. As such, if a patient is 59 or under, a 0.5 weighting factor is assigned to the age element, whereas a patient between the ages of 60 and 74 is assigned a 1.0 weighting to the age element. Finally, a patient 75 and older receives a 1.5 weighting factor to the age element.

Continuing with step 424, a determination is made as to the patient's body mass index (BMI) value, where different weighting factors may be assigned depending on the patient's BMI value in step 426. If the BMI value is greater than 30, then a 1.5 weighting factor is assigned to the BMI element. A BMI value between 25 and 29 will have a 1.0 weighting factor assigned to the BMI element, while a BMI value below 25 will have a 0.5 weighting factor assigned to the BMI element.

Subsequently, at step 428, the weighted values associated with the infection risk values are aggregated to create an infection risk assessment value for the patient as a percentage risk of infection. Process 400 shown in FIGS. 4A and 4B may also be explained by the following equation: Risk of Infection=(1.5×Major Diagnosis)+[(n) 1.0×Other Diagnosis]+(1.0×Surgery)+Age+BMI, where Age=(0.5×1) if the patient is 59 or younger, (1.0×1) if the patient is 60-74, or (1.5×1) if the patient is 75 or older; BMI=(1.5×1) if a patient's BMI is 30 or higher, (1.0×1) if a patient's BMI is 25-29, or (0.5×1) if a patient's BMI is less than 25. The exemplary weighting factors may be associated with relevant historical patient data and/or designated by a specific healthcare provider or health system as desired based on previous experience with infection risk assessments or in an effort to focus on certain clinical practices for infection risk control.

Figure 5:
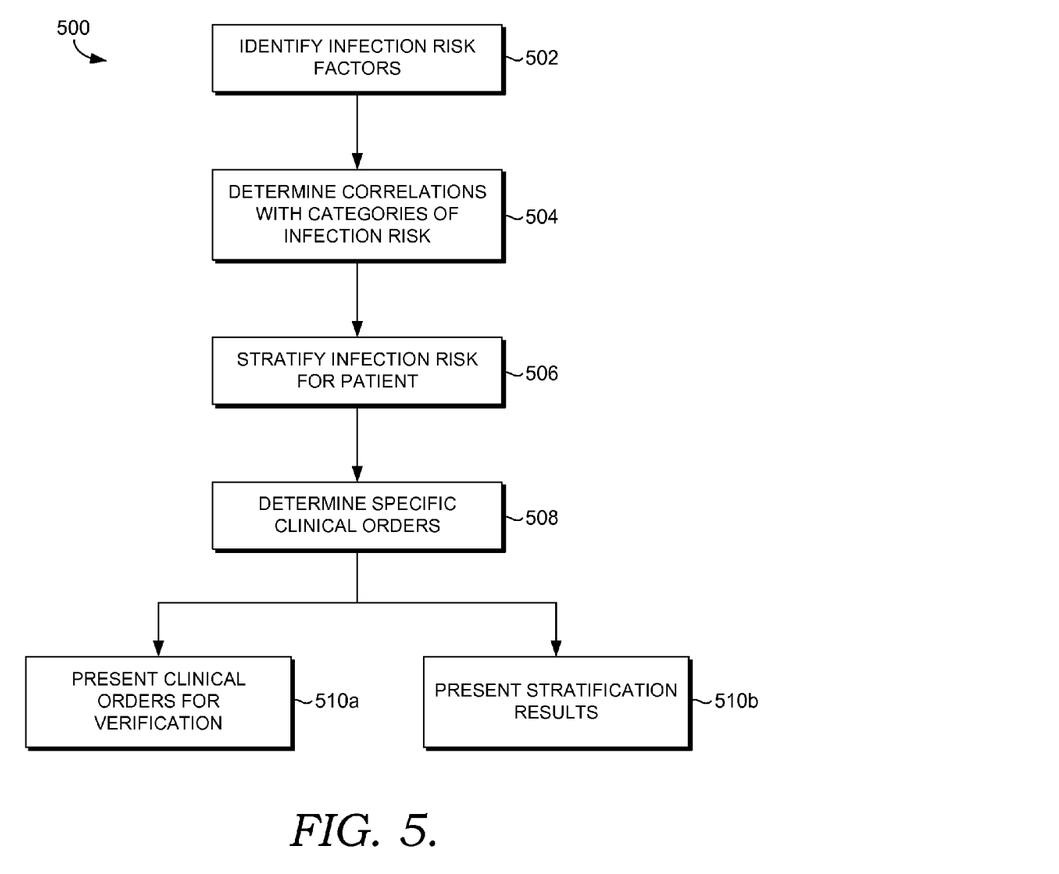
FIG. 5 is a flow chart representative of a process for invoking a clinical order for a particular patient based on an infection risk stratification.

Referring now to FIG. 5, a flow chart representative of a computerized method for invoking clinical orders for a particular patient based on an infection risk stratification is depicted generally as reference numeral 500. The method 500 may be implemented on the above-described exemplary medical information computing system 20 (FIG. 1).

According to the method 500, at step 502, infection risk factors for a particular patient are assessed. The infection risk factors may include any risk factors that are known to potentially cause an increased likelihood that an individual may acquire an infection, whether the individual is in an acute care setting, ambulatory setting, or any other setting where health services are provided or the individual is located after receiving health services. For instance, typical infection risk factors include those mentioned herein with respect to the infection risk determination method 200 depicted in FIG. 2.

It is then determined, at step 504, what correlations can be made between health data for the particular patient (e.g., from the patient's medical record) and multiple categories of infection risk associated with the infection risk factors. For instance, the infection risk categories may include, but are not limited to: infection risk due to tuberculosis, infection risk due to multidrug-resistant *Staphylococcus aureus* (MRSA), and infection risk due to Vancomycin-resistant *enterococcus* (VRE), or infection risk due to any other organism/pathogen of interest. As one example, a previously documented MRSA positive culture for a particular patient (particularly within a certain timeframe in the recent past) would correlate to an infection risk due to MRSA, but may or may not correlate to an infection risk due to VRE. As a further example, if a patient is documented to have the presence of decubitus ulcers upon admission to a care facility, there is a suggested correlation to multiple categories of infection risk (e.g., infection risk due to MRSA and VRE).

Based on the correlations between health data for the particular patient and multiple categories of infection risk, at step 506, the infection risk for the particular patient is stratified. The stratification involves attributing a level of concern for the different categories of infection risk. In one aspect, a weighting factor or score may be applied for each correlation due to the particular health data present for the patient and it's applicability to the associated infection risk category. Once all correlations are taken into account, at step 508, specific clinical orders relevant for the particular patient are determined based on the stratification risk. For instance, if it is determined that the overall infection risk due to MRSA is quite high based on all the correlations with data for the particular patient, a clinical knowledgebase (or other knowledge sources, such as those referenced with respect to infection risk determination method 200 herein) may be queried to find clinical orders that would be medically appropriate for the patient to mitigate the infection risk. By way of example only and not limitation, a clinical order may be for administration of a medication, a medical procedure (e.g., a diagnostic or laboratory test, surgical procedure to remove tissue around an infected site, etc.), initiation of a particular care protocol or set of protocols, or other medically relevant order.

Upon determining the clinical orders relevant for the particular patient based on the stratification risk, such orders are presented on a user interface of the medical information computing system 20 for verification by the appropriate clinician, at step 510a. The results of the infection risk stratification, from step 506, may also be presented on the user interface for the clinician, at step 510b. In one embodiment, the stratification results include the attributed overall level of concern for the different categories of infection risk, from step 506. In another embodiment, the stratification results include a list of each correlation between health data for the particular patient and multiple categories of infection risk associated with the infection risk factors, from step 504. Alternatively, the stratification results may include the list of correlations between health data for the particular patient and multiple categories of infection risk associated with the infection risk factors where such correlations exceed a preestablished threshold level of concern. Thus, the clinician would be presented with "key" correlations that indicate significant risk for a particular category. As one example, if the patient is documented to have severe combined immunodeficiency disease, then the system may highlight this particular information for clinician review, since it is an important (strong) indicator of infection risk due to MRSA.

As can be understood, embodiments of the present invention provide a computerized method and system for determining infection risk for a particular patient encountering a specific healthcare system. A user interface providing a graphical representation of the infection risk assessment at specific points in time while a patient is receiving care enables a clinician to visualize changes in infection risk over time, providing a better understanding of how a specific infection risk control plan may result in improved outcomes for the patient.

The present invention has been described in relation to particular embodiments, which are intended in all respects to be illustrative rather than restrictive. Alternative embodiments will become apparent to those of ordinary skill in the art to which the present invention pertains without departing from its scope. For example, in weighing the correlated risk factors, outcomes data for patients encountering specific providers or healthcare facilities may also be considered. This provides, in certain circumstances, further accuracy in the infection risk determination by considering additional patient-specific data, such as whether the patient has been at a location within a specific facility where drug-resistant organisms have been found.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and within the scope of the claims.

What is claimed is:

1. A computerized method carried out by a server running on one or more processors for invoking a clinical order for a particular patient based on an infection risk stratification, comprising:

selecting a set of benchmark infection risk factors for a particular patient based upon data associated with a particular healthcare facility treating the particular patient, data associated with a healthcare provider treating the particular patient, and data associated with one or more medical procedures being undertaken by the particular patient;

searching the particular patient's electronic medical record for patient-specific data related to the set of benchmark infection risk factors;

determining, using the one or more processors, correlations between the patient-specific data and two or more particular categories of infection risk associated with the set of infection risk factors, the correlations indicating a greater or lesser degree of infection risk probability resulting from the encounter between the particular patient and the healthcare provider, the procedure, and the particular healthcare facility;

determining one or more weighting factors to be applied to the two or more particular categories of infection risk, the one or more weighting factors being variably adjusted based on the degree of correlation between the patient-specific data and the two or more particular categories of infection risk and identity of the two or more particular categories of infection risk;

stratifying infection risk for the particular patient based on the correlations determined and the one or more weighting factors determined;

determining one or more specific clinical orders relevant for the particular patient based on the stratification of infection risk.

2. The method of claim 1, further comprising presenting the one or more specific clinical orders for verification by a clinician.

3. The method of claim 1, further comprising presenting results of the stratification of infection risk for the particular patient.

4. The method of claim 1, wherein the two or more particular categories of infection risk include infection risk due to tuberculosis and infection risk due to multidrug-resistant *Staphylococcus aureus* (MRSA).

5. The method of claim 1, wherein the one or more specific clinical orders relevant for the particular patient include one or more of administration of a particular medication, the one or more medical procedures, and a care protocol.

6. The method of claim 1, wherein the set of infection risk factors includes time since the particular patient was admitted to the healthcare facility.

7. The method of claim 1, wherein the two or more particular categories of infection risk include infection risk due to tuberculosis and infection risk due to Vancomycin-resistant *enterococcus* (VRE).

8. The method of claim 1, wherein the two or more particular categories of infection risk include infection risk due to multidrug-resistant *Staphylococcus aureus* (MRSA) and infection risk due to Vancomycin-resistant *enterococcus* (VRE).

9. The method of claim 1, wherein the set of infection risk factors includes locations within the healthcare facility where the particular patient has spent time.

10. The method of claim 1, wherein the set of infection risk factors includes the particular patient's overall length of stay at the healthcare facility.

11. The method of claim 1, wherein the set of infection risk factors includes the particular patient's length of intubation.

12. The method of claim 1, wherein the set of infection risk factors includes immunosuppressive conditions associated with the particular patient.

13. The method of claim 1, wherein the set of infection risk factors includes use of steroids by the particular patient.

14. The method of claim 1, wherein the set of infection risk factors includes chemotherapy protocols associated with the particular patient.

15. The method of claim 1, wherein the set of infection risk factors includes timing of prophylactic antibiotics administration prior to a surgical procedure.

* * * * *